US00PP30982P2

(12) United States Plant Patent
Ochiai

(10) Patent No.: US PP30,982 P2
(45) Date of Patent: Oct. 29, 2019

(54) ***CLEMATIS* PLANT NAMED 'KOKONOE'**

(50) Latin Name: ***Clematis* hybrid**
Varietal Denomination: Kokonoe

(71) Applicant: Koichiro Ochiai, Kanagawa (JP)

(72) Inventor: Koichiro Ochiai, Kanagawa (JP)

( * ) Notice: Subject to any disclaimer, the term of this patent is extended or adjusted under 35 U.S.C. 154(b) by 0 days.

(21) Appl. No.: 15/932,594

(22) Filed: Mar. 21, 2018

(30) Foreign Application Priority Data

Mar. 27, 2017 (QZ) ..... PBR 20170895

(51) Int. Cl.
*A01H 5/02* (2018.01)

(52) U.S. Cl.
USPC ..... Plt./228

(58) Field of Classification Search
USPC ..... Plt./228
See application file for complete search history.

*Primary Examiner* — Annette H Para
(74) *Attorney, Agent, or Firm* — Penny J. Aguirre

(57) ABSTRACT

A new cultivar of hybrid *Clematis*, 'Kokonoe', that is characterized by its unique flower shape with the tepals forming a star-shape and topped with numerous layers of tepaloids and a center of curled in tepaloids, its floriferous blooming habit, and its flowers that are a warm purple color with center tepaloids lighter purple in color.

2 Drawing Sheets

Botanical classification: *Clematis* hybrid.
Variety denomination: 'Kokonoe'.

BACKGROUND OF THE INVENTION

The present invention relates to a new and distinct cultivar of *Clematis*, botanically of hybrid origin, and will be referred to hereafter by its cultivar name 'Kokonoe'. 'Kokonoe' is grown as an herbaceous perennial for landscape use or as a terrace pot plant.

'Kokonoe' was derived from a breeding program conducted by the Inventor in Tokyo, Japan. The Inventor has made years of crosses between plants of *Clematis florida* (and other species now included in the Florida group of *Clematis*) and plants of *Clematis integrifolia*, and proprietary hybrids between them. The parental plants were unnamed and unpatented plants from the Inventor's breeding program and details on the exact parent plants are unavailable. 'Kokonoe' was selected by the Inventor as a single unique plant from a batch of seedlings in 2000.

Asexual propagation of the new cultivar was first accomplished by stem cuttings by the Inventor in Tokyo, Japan in 2000. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors. These attributes in combination distinguish 'Kokonoe' as a unique cultivar of *Clematis*.

1. 'Kokonoe' exhibits a unique flower shape with the tepals forming a star-shape and topped with numerous layers of tepaloids and a center of curled in tepaloids.
2. 'Kokonoe' exhibits a floriferous blooming habit.
3. 'Kokonoe' exhibits flowers that are a warm purple color with center tepaloids lighter purple in color.

'Kokonoe' can be most closely compared to the *Clematis* cultivars 'Vyvyan Pennell' (not patented) and 'Taiga' (U.S. Plant Pat. No. 27,591). 'Nyvyan Pennell' is similar to 'Kokonoe' in having flowers that are purple in color. 'Vyvyan Pennell' differs from 'Kokonoe' in having different flowers with broader and larger tepaloids that are lighter purple in color and in having a center with reproductive organs exposed. 'Taiga' is similar to 'Kokonoe' in having similar star-shaped, multi-layered flowers at the beginning of bloom. 'Taiga' differs from 'Kokonoe' in having a different flower shape at the end of bloom and tepaloid colors that are purple and tipped with yellow-green.

BRIEF DESCRIPTION OF THE DRAWINGS

The accompanying colored photographs illustrate the overall appearance and distinct characteristics of the new *Clematis*. The photographs were taken of a three-year-old plant of the new cultivar as grown in a greenhouse in a 5-liter container in Aalsmeer, The Netherlands.

The photograph in FIG. 1 provides a view of 'Kokonoe' in bloom.

Figure 1:
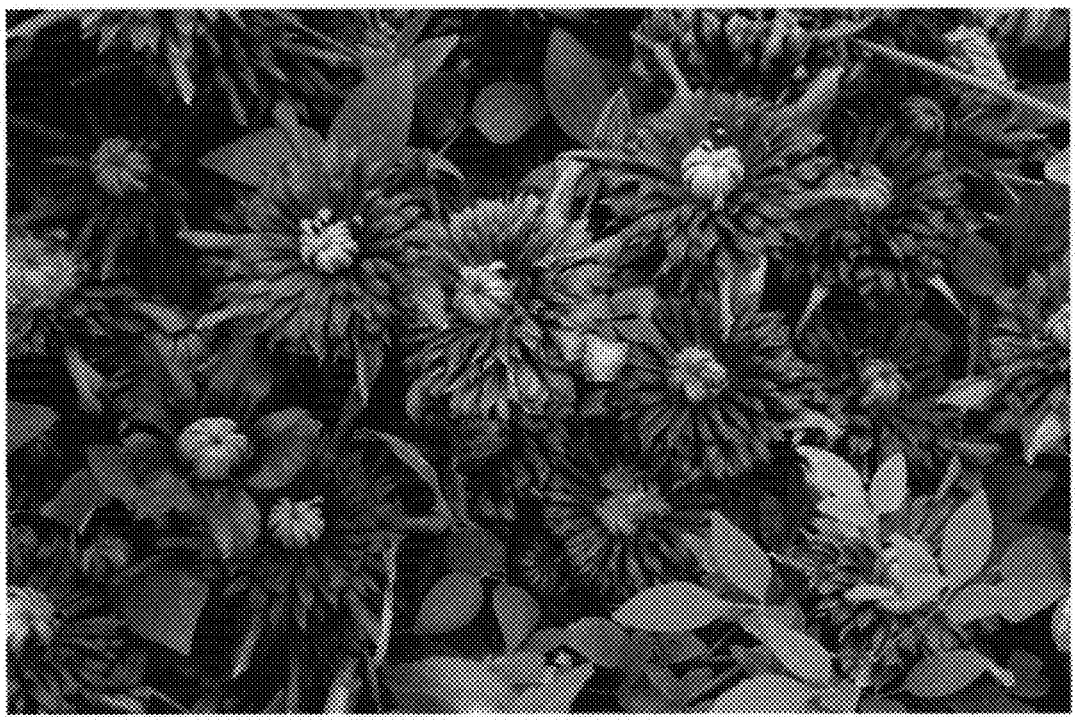
Figure 2:
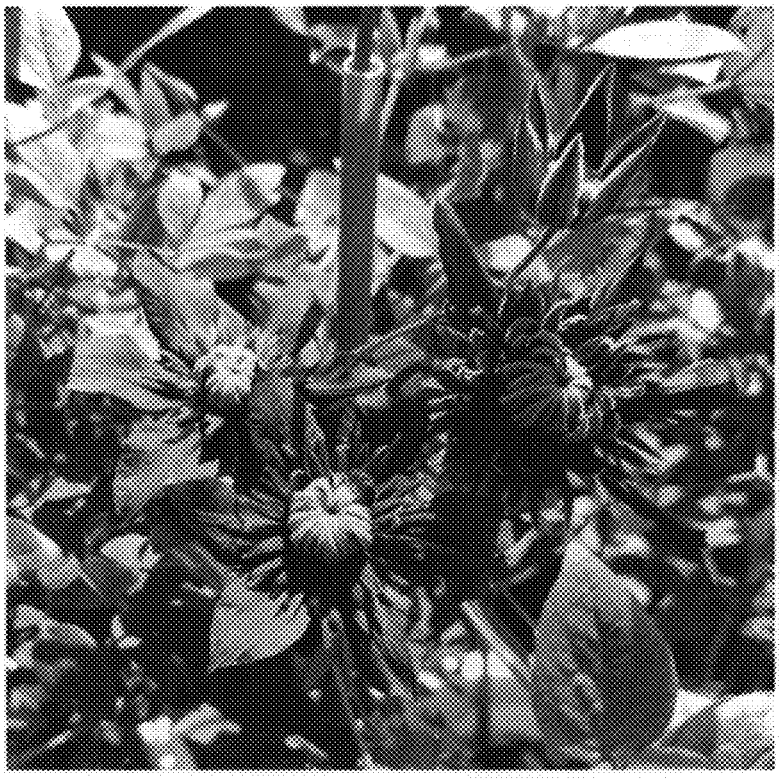
FIG. 2 provides a close-up view of the inflorescences of 'Kokonoe'.
Figure 3:
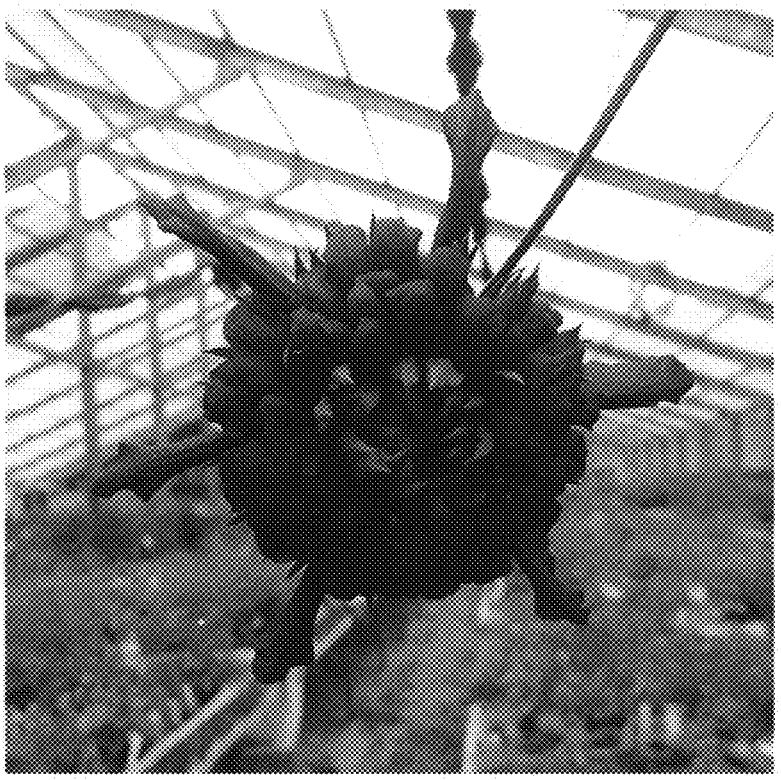

The photograph in FIG. 3 provides a view of a single inflorescence of 'Kokonoe'.

The colors in the photographs are as close as possible with the digital photography and printing techniques utilized and the color codes in the detailed botanical description accurately describe the new *Clematis*.

DETAILED BOTANICAL DESCRIPTION

The following is a detailed description of three-year-old plants of 'Kokonoe' as grown in a greenhouse in 5-Liter containers in Aalsmeer, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Blooms from late spring to early autumn in The Netherlands, blooms on new wood.

*Plant type.*—Deciduous perennial vine.

*Plant habit.*—Climbing with stems emerging from base.

*Height and spread.*—Reaching up to 25 m in height and up to 1.5 m in spread for 3-year-old plant pruned hard in winter.

*Cold hardiness.*—At least in U.S.D A. Zone 6.

*Diseases and pests.*—No unique susceptible or resistance to pests and diseases has been observed.

*Root description.*—Fleshy N167C in color with tips NN155D.

*Growth rate.*—Moderate, an average of 10 cm per month in spring.

*Propagation.*—Softwood stem cuttings from vegetative shoots.

*Root initiation.*—Roots develop in 6 weeks in summer under greenhouse conditions.

*Time required for root development.*—75 to 90 days to fully develop in a 5-cm container from a 5-cm cutting.

Stem description:

*Shape.*—Round with slightly 6 ribbed angles.

*Stem color.*—N77 A when young and 165D with bark 165A when mature.

*Stem size.*—Up to 2.5 m in length, an average of 3 mm in width.

*Stem surface.*—Sparsely short hairy when young and mature.

*Internode length.*—4 to 15 cm.

*Branching.*—From the base when pruned hard in winter.

*Stem strength.*—Strong and flexible.

Foliage description:

*Leaf arrangement.*—Opposite.

*Leaf division.*—Ternate.

*Leaf size.*—Up to 13 cm in length (including petiole) and up to 8 cm in width.

*Leaf attachment.*—Petiolate.

*Leaf shape.*—Ovate.

*Leaf fragrance.*—None.

*Leaflet shape.*—Lanceolate.

*Leaflet size.*—Up to 5 cm in length and 3 cm in width.

*Leaflet base.*—Terminal leaflet cuneate, side leaflet oblique.

*Leaflet apex.*—Acute.

*Leaflet venation.*—Pinnate and slightly reticulate, 137D in color on upper surface, 138B in color on lower surface, surface very short hairy.

*Leaflet quantity.*—3.

*Leaflet margin.*—Entire and occasionally with 1, 2 or 3 teeth.

*Leaflet surface.*—Upper and lower surface; a few sparse hairs.

*Leaf color.*—Upper and lower surface when young 144A, upper surface when mature 137B, lower surface when mature 138B.

*Petioles.*—3 to 4 cm in length, 0.8 mm in diameter, 1437B in color and sometimes flushed with N77B, round in shape and slightly canaliculate on upper surface and articulate towards leaflets, surface sparsely hairy, aspect typically straight and sometimes curling.

*Petiolules.*—Terminal leaflet 5 mm to 1.5 cm in length and 7 mm in diameter, side leaflets up to 7 mm in length and 7 mm in width, round in shape, surface sparsely hairy, 137B in color, straight and sometimes curly.

Inflorescence description:

*Inflorescence type.*—Solitary or a 3-flowered dichasial cyme.

*Inflorescence arrangement.*—Axillary on young shoots in summer.

*Peduncles.*—Round in shape, 4 to 8 cm in length, 1.5 mm in width, 146A in color tinted with N77D in color, surface sparsely hairy.

*Pedicels.*—Round in shape, 7 to 12 cm in length, 1.2 mm in diameter, 146A in color tinted with N77D in color, surface sparsely hairy and more densely hairy towards the flower.

*Flower buds.*—Outward but upright before opening, ovate in shape, up to 2 cm in length and 1 cm in diameter, 144A in color with veins N92A, surface glabrous with pubescent seams N187C in color.

*Flower fragrance.*—None.

*Lastingness of the flowers.*—Individual flowers last about 15 days.

*Flower quantity.*—20 to 40 per stem.

*Flower type.*—Rotate, spreading and filled (double-like) with tepaloids.

*Flower aspect.*—Outward and upright.

*Flower shape.*—Slightly flattened when open.

*Flower size.*—Up to 10 cm in diameter and 2 cm in depth.

*Bracts.*—Simple, lanceolate in shape, up to 3.5 cm in length and 2 cm in width, acute apex, entire margin but cleft at base, cuneate-oblique base, color 137B on upper surface and 138B on lower surface, veins have a few short hairs on both surfaces and are 137D in color on upper surface and 138B in color on lower surface, both surfaces are sparsely hairy.

*Flower receptacle.*—Average of 3 mm in diameter, hairy surface, 146A in color.

*Tepal number.*—4 to 6.

*Tepal shape.*—Oblanceolate.

*Tepal aspect.*—Flat when opening becoming folded lengthwise and then quickly caducous.

*Tepal apex.*—Acute.

*Tepal base.*—Cuneate, not overlapping.

*Tepal margin.*—Entire.

*Tepal surface.*—Upper surface; glabrous, lower surface; margin pubescent, middle section glabrous with sparsely hairy veins.

*Tepal color.*—Upper surface; when opening N83B with base 193C with spots of 85D, when mature 83A with veins 79A and 85C towards base with very base 193B, lower surface; when opening 144A with veins N92C, when mature 86A with pubescence N187C, middle section 144B with veins 86A.

*Tepal size.*—Up to 4.5 cm in length 2.2 cm in width.

*Tepaloid number.*—150 to 250.

*Tepaloid shape.*—Small oblanceolate.

*Tepaloid aspect.*—Spreading with apex bending downward.

*Tepaloid apex.*—Acute.

*Tepaloid base.*—Cuneate.

*Tepaloid margin.*—Entire.

*Tepaloid surface.*—Upper surface; glabrous, lower surface; pubescent.

*Tepaloid color.*—Upper and lower surface; N83A with base 84D and very base 193B.

*Tepaloid size.*—Up to 2.5 cm in length and 8 mm in width.

Reproductive organs:

*Gynoecium.*—None.

*Androecium.*—None.

*Seed.*—None, no reproductive organs.

It is claimed:

1. A new and distinct cultivar of *Clematis* plant named 'Kokonoe' as herein illustrated and described.

* * * * *